(12) United States Patent
Lasser et al.

(10) Patent No.: US 7,370,534 B2
(45) Date of Patent: May 13, 2008

(54) MULTIANGLE ULTRASOUND IMAGER (75) Inventors: Robert S. Lasser, Washington, DC (US); Marvin E. Lasser, Potomac, MD (US); John W. Gurney, Great Falls, VA (US)

(73) Assignee: Imperium, Inc., Silver Spring, MD (US)

( * ) Notice: Subject to any disclaimer, the term of this patent is extended or adjusted under 35 U.S.C. 154(b) by 293 days.

(21) Appl. No.: 11/087,854

(22) Filed: Mar. 24, 2005

(65) Prior Publication Data

US 2006/0213273 A1    Sep. 28, 2006

(51) Int. Cl.
*G01N 29/06* (2006.01)
*G01N 29/26* (2006.01)
*G01N 29/27* (2006.01)

(52) U.S. Cl. ............................. 73/602; 73/620; 73/621; 73/625

(58) Field of Classification Search ................. 73/606, 73/620, 602
See application file for complete search history.

(56) References Cited

U.S. PATENT DOCUMENTS

| | | | | |
|---|---|---|---|---|
| 3,996,792 A | * | 12/1976 | Kubota et al. ................. | 73/611 |
| 4,258,574 A | * | 3/1981 | Hildebrand et al. ........... | 73/625 |
| 5,307,680 A | * | 5/1994 | Drescher-Krasicka ........ | 73/606 |
| 5,483,963 A | | 1/1996 | Butler et al. | |
| 5,549,003 A | * | 8/1996 | Drescher-Krasicka ........ | 73/606 |
| 5,955,671 A | * | 9/1999 | Gilmore et al. ............... | 73/597 |
| 6,552,841 B1 | | 4/2003 | Lasser et al. | |

FOREIGN PATENT DOCUMENTS

JP          04136755 A   *   5/1992

OTHER PUBLICATIONS

"Nondestructive Testing Handbook", Second Edition, vol. 7 (Ultrasonic Testing), Chapter 2 (pp. 205-209), Chapter 4 (pp. 214-217), Chapter 8 (pp. 249-257), *American Society for Nondestructive Testing*.

* cited by examiner

*Primary Examiner*—John E. Chapman
*Assistant Examiner*—Rose M Miller
(74) *Attorney, Agent, or Firm*—Buchanan Ingersoll & Rooney PC (57) ABSTRACT

Systems and methods to obtain an ultrasonic image of a large detection area are disclosed. A system includes a source of ultrasound generating ultrasonic energy and projecting the ultrasonic energy from a projecting end and an adapter interfaced to the projecting end and ultrasonically coupling the source of ultrasound to a first surface of the structure to be imaged at an adjustable angle of incidence. A method includes ultrasonically coupling a source of ultrasonic energy to a first surface of a structure to be imaged with an adapter, the adapter adjustable to a select a first angle of incidence and a second angle of incidence, projecting ultrasonic energy into the structure, and detecting a reflected acoustic energy from the structure with an ultrasound camera. A first angle of incidence is selected to introduce a longitudinal wave into the structure, and a second angle of incidence is selected to introduce a shear wave into the structure.

29 Claims, 10 Drawing Sheets

MULTIANGLE ULTRASOUND IMAGER

FIELD

The present disclosure is directed to a method and apparatus to obtain a real time C-scan image of a large detection area, e.g., a single image having a detected field of view of a large area.

BACKGROUND

A common application of ultrasound is for the detection of cracks, corrosion and other similar flaws in metals and welded structures. A particular need is to detect flaws in welded structures. These flaws include such things as lack of fusion planes, porosity, inclusions, and other similar flaws that may compromise the structural integrity of the welded part. The majority of contact testing employs longitudinal waves propagating normal to the test object surface. However, there is often a need for employing shear waves propagating at an angle, for example, for imaging surfaces substantially parallel to the test object surface, discontinuities in weld bevels, e.g., welds with countersinks, or other uneven top surfaces.

Many ultrasound imaging studies have been carried out on welds. A particularly good set of images have been presented in Chapter 4 of *Nondestructive Testing Handbook*, Second Edition, Volume Seven on Ultrasonic Testing, the disclosure of which is incorporated herein by reference. Images are shown of welds that have regions with a lack of fusion, regions of welds with porosity, and welds showing regions of discontinuities as well as regions of intergranular stress corrosion cracks.

Fatigue failures occur in those locations that are subjected to repeated high stress loadings and are usually associated with areas having stress concentrations, e.g., around fasteners. For example, in the areas around a flat head rivet, the base material features a countersunk hole to accept the rivet head. This countersink leads to several "knife edges" (e.g., the rivet opening with walls normal to the structure surface) that serve to further increase the normal stress concentration caused by the hole alone and thus are particularly prone to fatigue failures. These failures typically begin as a crack that is initiated at one of the knife-edges that then progresses with repeated loading The prediction of any fatigue crack is an extremely complex combination of stress history and material properties with a large statistical variation expected even under perfect laboratory conditions. Thus, one way to ensure that no cracks are present is to perform an inspection of fasteners in the highly stressed areas, e.g., in highly stressed areas of the airframe.

Present inspection methods employ an ultrasonic testing (UT) transducer. For example, typical portable ultrasound devices allow the operator to make determinations about internal defects by sending out an ultrasound pulse and studying the amplitude and time of returned pulses. In another example, an ultrasonic testing (UT) transducer that is slowly rotated around a fastener can develop a map of the full 360° region. Since a focused beam transducer is used, only a single pencil-point region is checked at a time, and consequently the whole process takes on the order of minutes per fastener. Further, the direct test results (before any post-processing) are signal responses that require an experienced operator to interpret correctly. The combination of long inspection times and high operator skill requirements can limit the overall probability of detection of any cracks or flaws.

SUMMARY

An exemplary system to obtain an ultrasonic image of a large detection area of a structure to be imaged comprises a source of ultrasound, an imaging array comprising a two dimensional array of acoustic to electrical transducers which produce electrical signals in response to an acoustic beam received by the imaging array, and an adapter ultrasonically coupling the source of ultrasound to a first surface of the structure to be imaged at an adjustable angle of incidence. A first angle of incidence is selected to introduce a longitudinal wave into the structure, and a second angle of incidence is selected to introduce a shear wave into the structure.

An exemplary method of ultrasonic imaging a structure comprises ultrasonically coupling a source of ultrasonic energy to a first surface of a structure to be imaged with an adapter, the adapter adjustable to a select a first angle of incidence and a second angle of incidence, projecting ultrasonic energy into the structure, and detecting a reflected acoustic energy from the structure with an ultrasound camera, the ultrasound camera including an imaging array comprising a two dimensional array of acoustic to electrical transducers which produce electrical signals in response to the acoustic energy received by the imaging array. The detected acoustic energy produces a real time C-scan image of a detection area equal to or larger than one square inch. The first angle of incidence is selected to introduce a longitudinal wave into the structure, and the second angle of incidence is selected to introduce a shear wave into the structure.

BRIEF DESCRIPTION OF THE DRAWING FIGURES

The following detailed description of preferred embodiments can be read in connection with the accompanying drawings in which like numerals designate like elements and in which.

DETAILED DESCRIPTION

The present application is directed to a method and apparatus to obtain a real time C-scan image of a large detection area, e.g., a single image having a detected field of view of a large area. As used herein, large area and large detection area means an area equal to or larger than one square inch, preferable an area equal to or larger than two square inches, and more preferable an area of about three to four square inches. The method and apparatus can also be extended to create a C-scan image of a large area, albeit not in real-time, by forming a composite image of multiple collected images. As used herein, A-scan refers to ultrasonic imaging techniques using single point returns and C-scan image refers to ultrasonic imaging techniques using parallel plane view. Ultrasound may also be collected in B-scan, which herein refers to ultrasonic imaging techniques using a perpendicular view.

Figure 1:
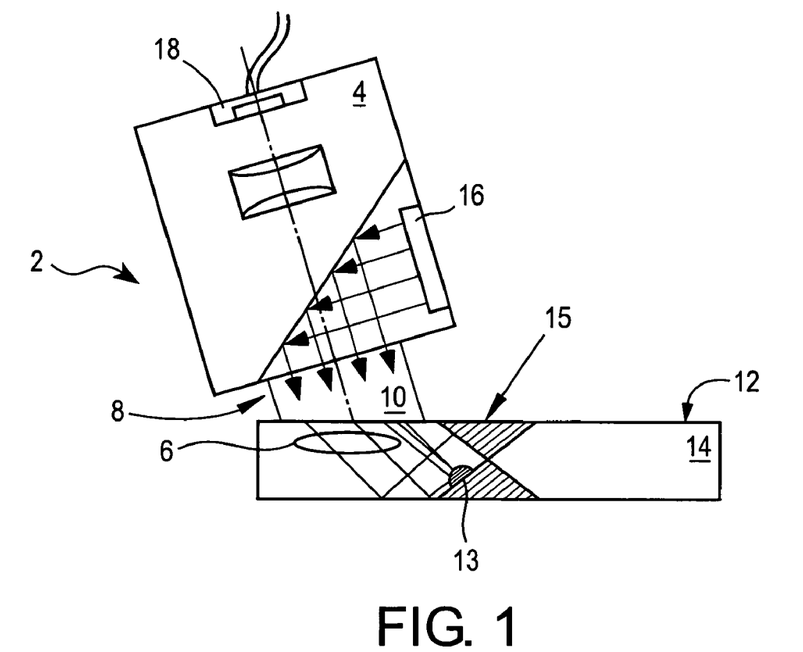
FIG. 1 shows an exemplary embodiment of an apparatus to obtain an ultrasonic image of a large detection area of a structure to be imaged.

An exemplary embodiment of an apparatus to obtain an ultrasonic image of a large detection area of a structure to be imaged is shown in FIG. 1. In the exemplary embodiment illustrated, the apparatus 2 comprises an ultrasound camera 4 generating ultrasonic energy and projecting the ultrasonic energy 6 from a projecting end 8 and a shear wave adapter 10 interfaced to the projecting end 8 and capable of ultrasonically coupling the ultrasound camera 4 to a first surface 12 of the structure 14 to be imaged to obtain an adjustable angle of incidence $\theta_1$. The ultrasound camera 4 includes a first transducer 16 for generating an unfocused acoustic beam and an imaging array 18 comprising a two dimensional array of acoustic to electrical transducers which produce electrical signals in response to an acoustic beam received by the imaging array 18. Also shown in FIG. 1 is a weld discontinuity 13 at a weld, such as the illustrated double bevel weld 15.

Figure 2:
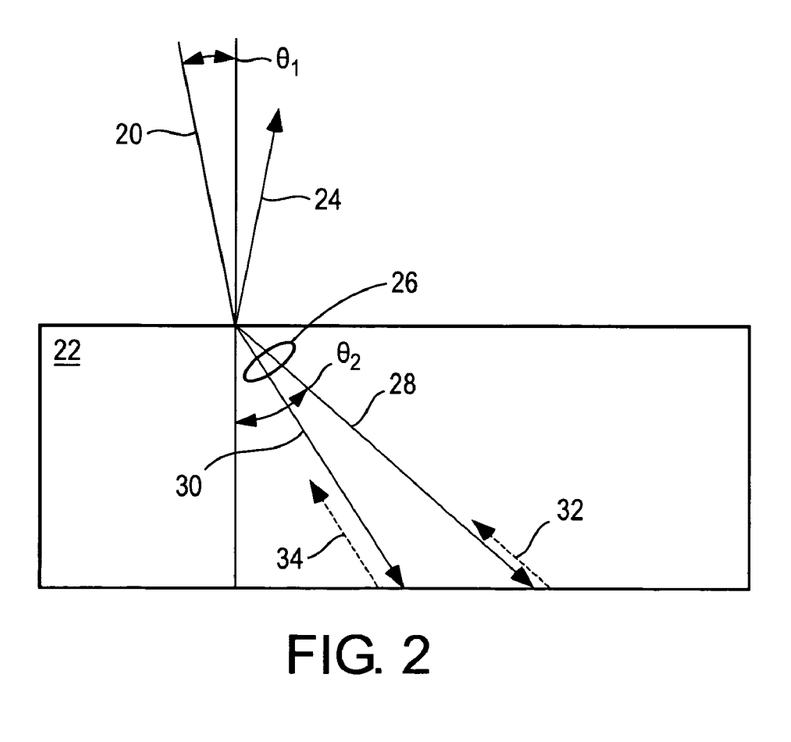
FIG. 2 illustrates the modes that occur when ultrasound is impinged onto a structure, such as a steel or aluminum plate.

When ultrasound energy strikes a part at an oblique angle, it is possible to generate a number of possible waves. FIG. 2 shows an incident wave 20 striking a structure 22 (in this case aluminum). Here, the incident wave 20 comes in at some angle $\theta_1$ to the structure 22. A portion 24 of this energy is reflected off, while a portion 26 enters the structure 22. The portion that enters the structure 22 can be either a longitudinal wave 28 or a shear wave 30. The ability to support these different modes is a function of the angle $\theta_1$ and the two materials' acoustic properties. Also shown in FIG. 2 are a scattered longitudinal wave 32 and a scattered shear wave 34.

Figure 3:
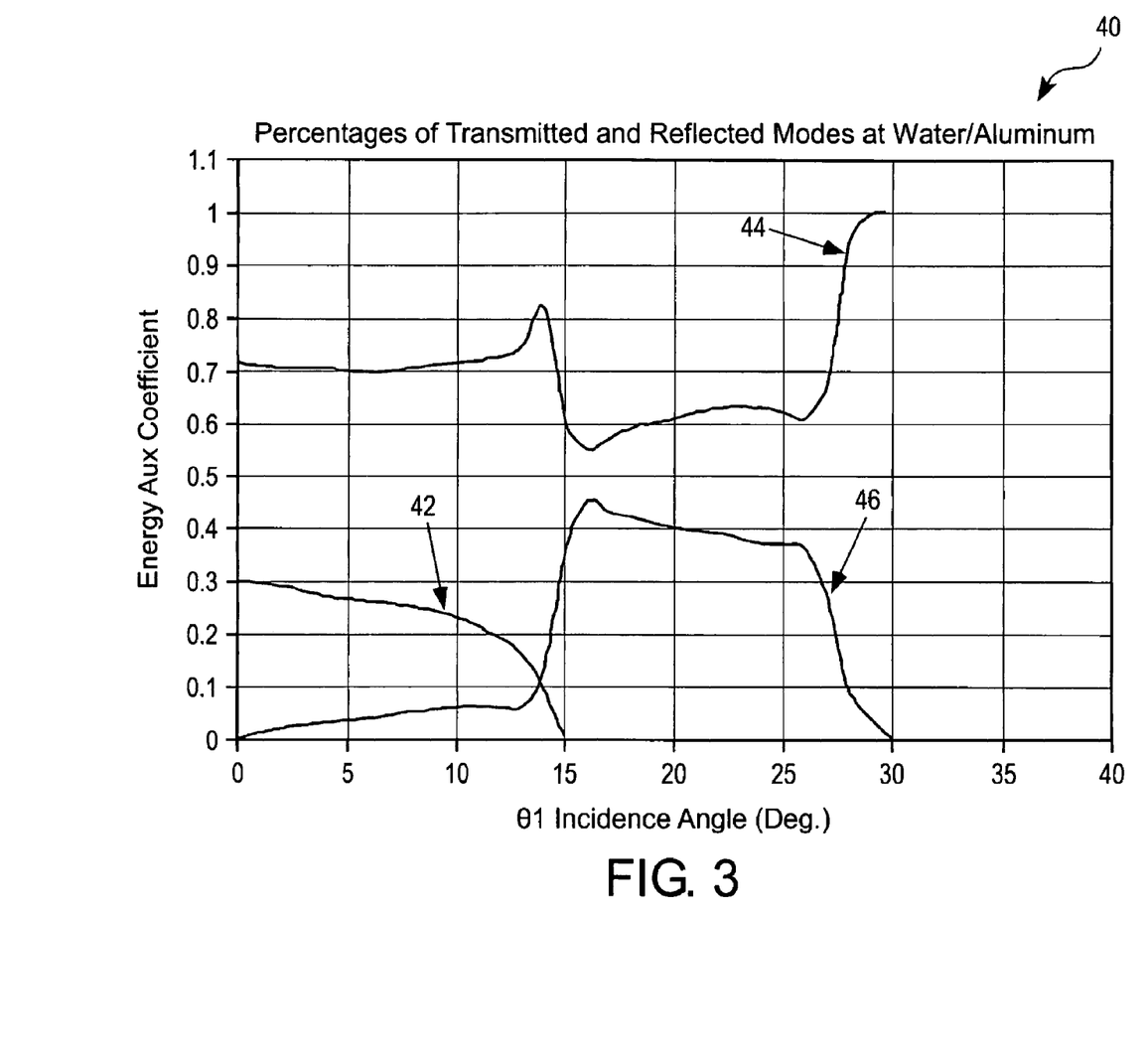
FIG. 3 graphically illustrates percentages of transmitted and reflected energy at an exemplary interface of a structure where the materials are water and aluminum.

The relationship for water and aluminum is shown in the graph in FIG. 3. Thus, for an angle of $\theta_1=0°$, approximately 70% of the energy is reflected off of the front surface and approximately 30% is transmitted into the part as a longitudinal wave. Beyond an angle of approximately 15°, there is no longitudinal energy transmitted into the plate, and the portion of shear wave energy begins to increase markedly. Here, the exemplary interface is the water/aluminum interface and the graphical representation 40 includes a transmitted longitudinal wave 42, a reflected longitudinal wave 44, and a transmitted shear wave 46. As shown in FIG. 3, once the angle of incidence (or $\theta_1$) is equal to or greater than about fifteen degrees, no transmitted longitudinal wave is generated in the structure. Also, the percentage of energy transmitted by the shear wave begins to rapidly increase at about thirteen degrees and becomes greater than the transmitted longitudinal wave at an angle of incidence of about fourteen degrees. At an angle of incidence of about thirteen degrees to fourteen degrees, the transmitted shear wave becomes greater than the transmitted longitudinal wave and, beginning in this range and for purposes of ultrasonic imaging as disclosed herein, there is substantially no transmitted longitudinal wave generated in the structure. Further and as shown in FIG. 3, the energy of the reflected longitudinal wave is near or at a minimum in a range of incidence angles that substantially corresponds to the range of incidence angles at which the energy of the transmitted shear wave is near or at a maximum. Thus, the contribution of reflected longitudinal wave energy to the imaging process is also near or at a minimum, increasing the sensitivity and resolution of the imagining using the transmitted shear wave. Similar relationships to that shown in FIG. 3 can be determined for other materials.

From the above, specific angles can be calculated for different material combinations based upon the acoustic properties of the materials involved, and acoustic relationships such as Snell's law. For all materials, the maximum transmitted longitudinal wave occurs at $\theta_1=0°$.

It is to be appreciated that the angle of incidence $\theta_1$ varies as a function of the test material and it is advantageous to be able to vary the testing parameters, including the angle of incidence, during the test to maximize the imaging results. Assuming that the incident longitudinal wave is propagated through water, the transmitted angle maximizes for aluminum at $\theta_1$ approximately 16.5° and for steel at $\theta_1$ approximately 18°. In some exemplary embodiments, the adjustable angle of the shear wave adapter is adjusted such that an incident wave of ultrasonic energy maximizes the shear energy in the structure, e.g., an angle of incidence $\theta_1$ of greater than or equal to fifteen degrees. In preferred embodiments, the angle of incidence $\theta_1$ is from about sixteen degrees to thirty degrees, more preferable from about sixteen to twenty-six degrees and most preferably from about sixteen to twenty degrees.

The acoustic camera, when operated for example in the pulse echo mode, relies on scattered energy from the signals that are transmitted into the part to create an image. In some cases, the most information can be obtained from energy scattered from longitudinal waves, while in other cases, shear waves are preferable. Having a camera that can adjust $\theta_1$ from 0° to 20° provides the flexibility required in this area. In some exemplary embodiments, the shear wave adapter angles the ultrasound camera relative to the structure to introduce shear and/or longitudinal waves into the structure. For example, a first angle of incidence can selected to introduce a longitudinal wave into the structure, and a second angle of incidence can be selected to introduce a shear wave into the structure. In some exemplary embodiments, the shear wave adapter angles the ultrasound camera relative to the structure such that substantially only shear waves are introduced into the interior of the structure.

In an exemplary embodiment, the angled surface of the shear wave adapter is adjustable. For example, a worm screw can be used to increase or decrease the angle of the angled surface by clockwise or counterclockwise rotation. Of course other devices to adjust the angle of the angled surface can be utilized. In an exemplary embodiment, one may select a constant value for the angle of the angled surface that will work sufficiently effectively for several materials. For example, an angle of 17° will work sufficiently effectively to obtain an ultrasonic image of a large detection area of a structure to be imaged where the structure is formed of steel or aluminum.

In an exemplary embodiment, the ultrasound camera can be stationary or can be positioned at an angle of incidence as disclosed herein and optionally rotated about a fixed axis while the shear waves are directed into the structure.

Figure 4A:
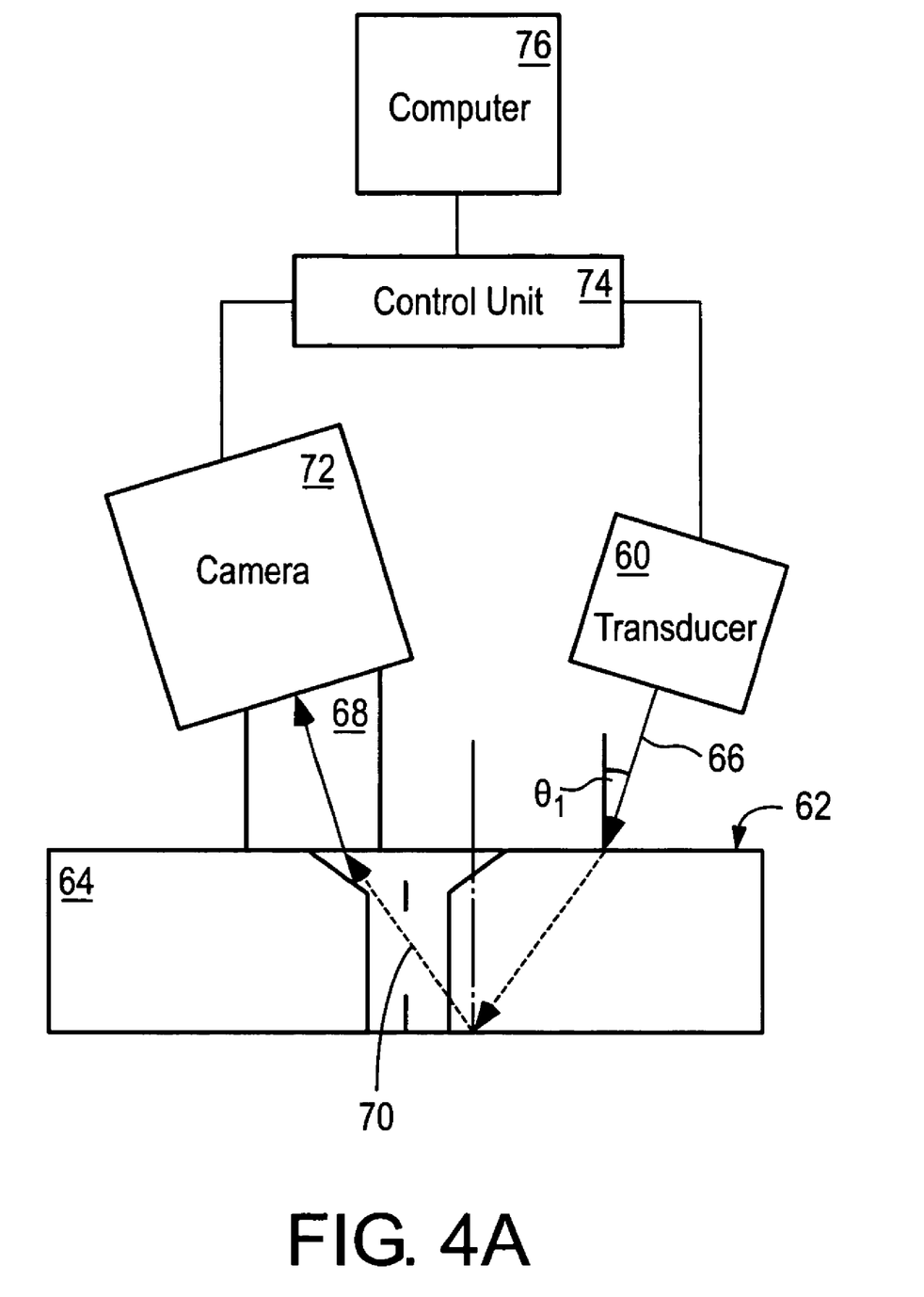
FIGS. 4A and 4B show exemplary positions for a source of ultrasound and an ultrasound camera schematically illustrated in pitch-catch mode (FIG. 4A) and pulse-echo mode (FIG. 4B).
Figure 4B:
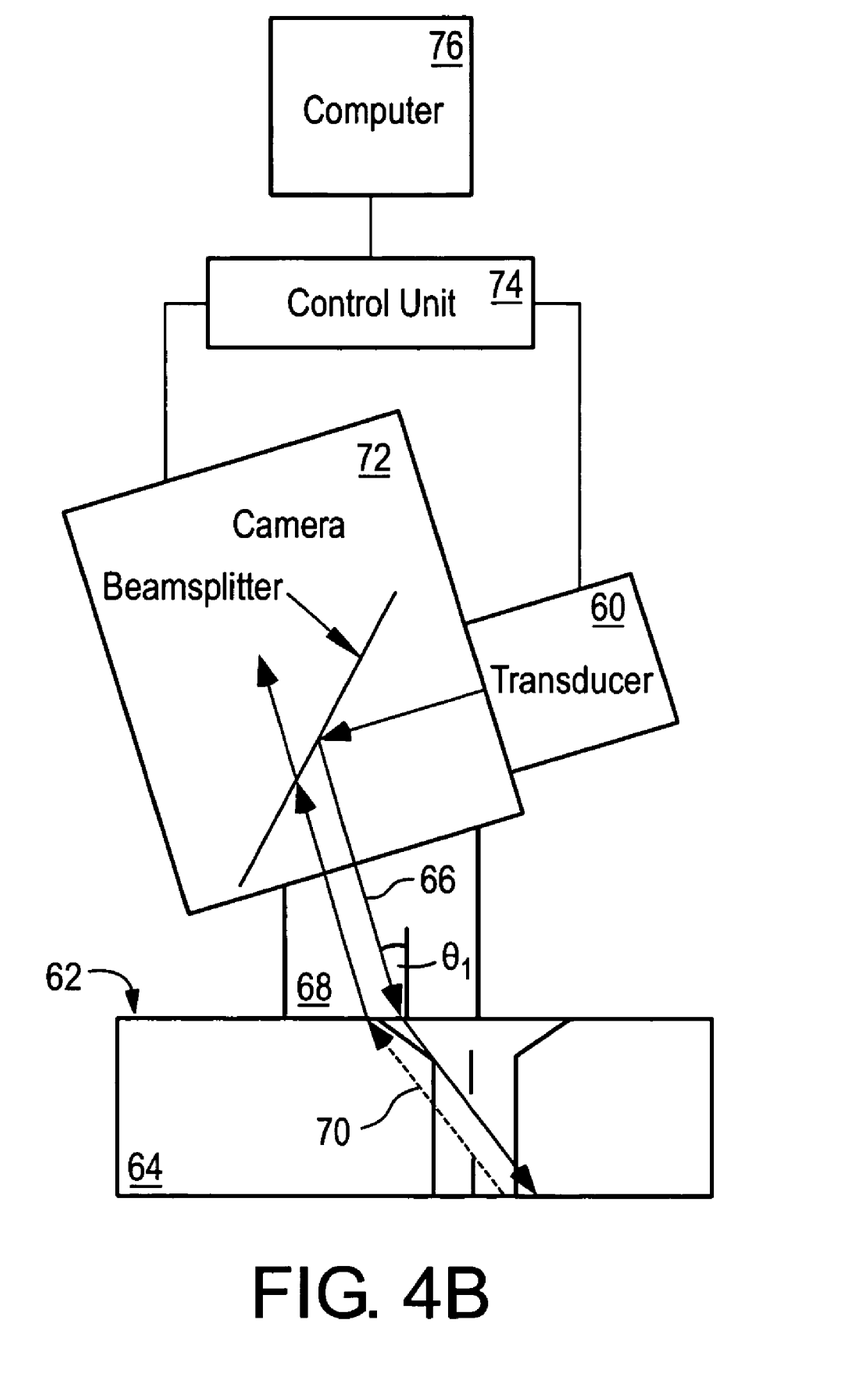

Either a pitch-catch mode, e.g., the source of ultrasonic energy and the ultrasound camera are positioned separate from each other as shown schematically in FIG. 4A, or a pulse-echo mode, e.g., the source of ultrasonic energy is incorporated with the ultrasound camera as shown schematically in FIG. 4B, can be used. In pulse echo mode, one embodiment of the ultrasound camera includes a beam splitter that directs the ultrasonic energy from the source of ultrasonic energy towards the first surface of the structure and passes reflected shear wave from the structure toward a detecting surface of the ultrasound camera, as disclosed and discussed in U.S. Pat. No. 6,552,841, the entire disclosure or which is herein incorporated by reference.

In the exemplary embodiments of FIGS. 4A and 4B, a source of ultrasonic energy 60, such as a transducer, generates ultrasonic energy, which is directed toward a first surface 62 of a structure 64, such as an aluminum structure with a countersunk fastener hole. The generated ultrasonic energy is represented by incident wave 66. Incident wave 66 is coupled to the first surface 62 of the structure 64 at a first angle $\theta_1$, also called an angle of incidence, by an adapter 68. The first angle $\theta_1$ is sufficient to enhance and/or maximize the detection of a reflected shear wave 70 in the structure 64.

As shown in FIGS. 4A and 4B, the ultrasound camera 72 and the source of ultrasonic energy 60 can optionally be integrated with a control unit 74 and a computer 76, forming, for example, a computer controlled imaging system that has a scanning feature. The computer allows for viewing the ultrasonic image, e.g., viewing an image on a LCD, a monitor, or a computer monitor. In exemplary embodiments, the ultrasound camera and the adapter are part of a hand held device having an integrated viewing screen.

The first angle $\theta_1$ can be achieved by interfacing a shear wave adapter to a projecting end of the source of ultrasonic energy. The shear wave adapter can be as described herein. For example, the shear wave adapter can have an adjustable angled surface, e.g., the angle of incidence is selectable, or may have a constant value for the angle of the angled surface that will work sufficiently effectively for several materials. In exemplary embodiments, the angle of incidence substantially eliminates a transmitted longitudinal wave. In some exemplary embodiments, the angle of incidence can be adjusted from zero degrees to about thirty degrees. In such an adjustable system, the camera can be used to introduce both longitudinal and shear energy into the part, thus providing more inspection flexibility.

In a further embodiment, both shear wave and time range-gating techniques are used in combination to detect features such as cracks, corrosion and discontinuities in a structure. The apparatus and methods disclosed herein can be used to collect these images in real-time over a relatively large area. The combination method permits the user to more easily discriminate between returns from various regions of the test object.

Figure 5:
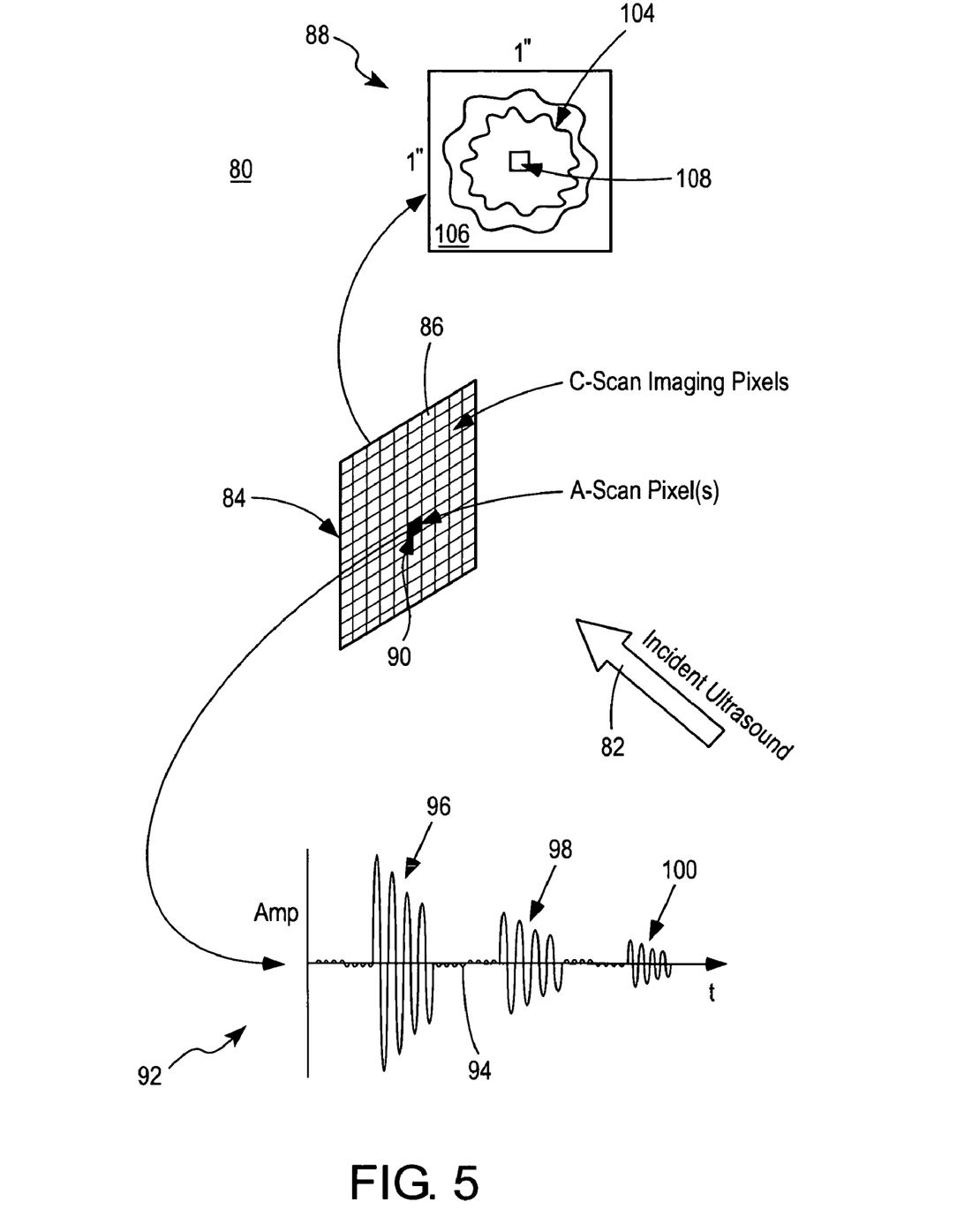
FIG. 5 schematically illustrates detection signals generated by the ultrasound interaction with the imaging array.

An exemplary embodiment of systems and methods to obtain an ultrasonic image of a large detection area uses both C-scan and A-scan to obtain an image. For example, the ultrasound camera disclosed herein can obtain a real time A-scan image of a portion of the large detection area. In exemplary embodiments, the portion of the large detection area is a central portion of the large detection area. Further, an array incorporated into the camera can obtain a C-scan image produced from a first detection signal from a first group of pixels of the imaging array and can also obtain an A-scan image produced from a second detection signal from a second group of pixels of the imaging array. FIG. 5 schematically illustrates the detection signals generated by the ultrasound interaction with the imaging array. In the FIG. 5 exemplary embodiment 80, incident ultrasound 82 from a structure impinges on the imaging array 84. The imaging array includes a plurality of pixels. A portion 86 of the plurality of pixels produce a first detection signal that is processed to form a C-scan image 88. A different portion 90 of the plurality of pixels produce a second detection signal that is processed to form a A-scan image 92. The A-scan image 92 is shown as a signal 94 with amplitude plotted as a function of time, for example as an oscilloscope image. A first response 96 on the A-scan signal 94 is, for example, a front surface of the structure; a second response 98 on the A-scan signal 94 is, for example, a middle surface flaw of the structure; and a third response 100 on the A-scan signal 94 is, for example, a rear surface of the structure. FIG. 5 also shows a C-scan image 88 as an image 104 on a viewing screen 106, such as a LCD, a monitor, or a computer monitor or an integrated viewing screen of a hand held device. Note that a portion 108 of the image 104 is missing. This portion 108 correlates to those portion of pixels that produce a second detection signal that is processed to form the A-scan image 92.

EXAMPLE ONE

Figure 6A:
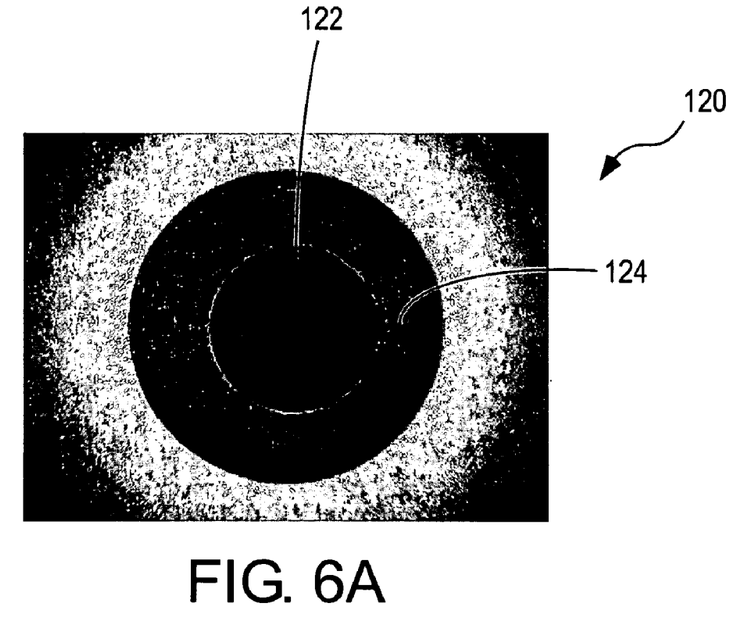
FIGS. 6A and 6B shows a test target used in a test of an exemplary method and apparatus to obtain an ultrasonic image.
Figure 6B:
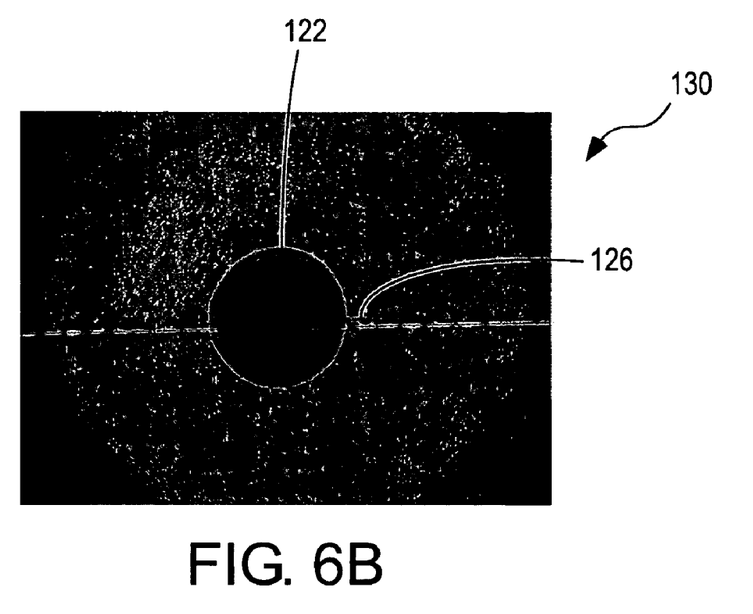

Pitch-catch mode; aluminum structure; coupling medium water; angle of incidence was about twenty degrees. All tests were done using a 5 MHz transducer and driven by a Ritec Model BP-9400 pulser. The aluminum structure included man-made flaws including holes with small (≈0.005 inch wide×0.040 inch long) cracks that have been machined into the plate. FIG. 6A is a frontside image 120 of the aluminum structure showing a hole 122 and a frontside crack 124. FIG. 6B is a backside image 130 of the aluminum structure showing the hole 122 and a backside crack 126. The test simulates ultrasound tests for the T-38 and F-5 aircraft.

Figure 7:
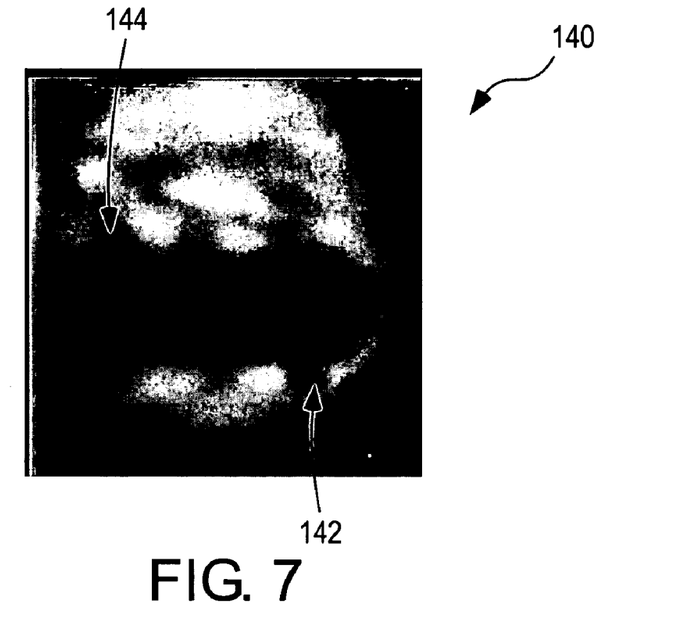
FIG. 7 is an image showing the cracks for a square hole (i.e., no countersink). Both a frontside crack and a backside crack are shown.

In a first part, the hole without a fastener installed was examined. FIG. 7 is an image 140 that shows the cracks for a square hole (i.e., no countersink). Both a frontside crack 142 and a backside crack 144 are shown. The image 140 in FIG. 7 clearly show the triangular cracks or side protrusions that are visible in ultrasound images when the crack profile is orthogonal to the plane formed by the axes of the transducer and camera. The image of either the front or backside crack can be brought more clearly into focus by adjusting the camera lens setting.

Figure 8:
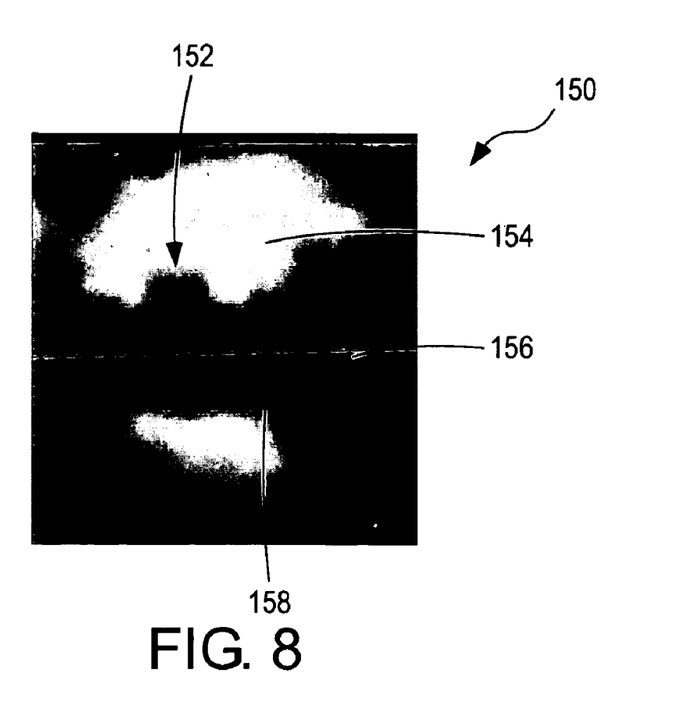
FIG. 8 is an image showing the cracks for a flat-head bolt installed in a countersunk hole in the test target. The nut on this bolt was covered with tape so that the region around the rear side of the plate was air-backed.

In a second part, a flat-head bolt was installed in a countersunk hole. To further simulate a real-world situation, the nut on this bolt was covered with tape so that the region around the rear side of the plate was air-backed, as would typically be encountered in a real-world case. The image 150 shown in FIG. 8 includes the backside crack 152. Note that the backside crack 152 is in a shadow zone 154 formed below the head 156 of the countersunk flat-head bolt 158.

EXAMPLE TWO

Pulse-echo mode; aluminum structure; coupling medium water; angle of incidence was about twenty degrees. All tests were done using a 5 MHz transducer and driven by a Ritec Model BP-9400 pulser. In this example, an ultrasound camera with a beam splitter was used. An example of a suitable ultrasound camera with a beam splitter is described in U.S. Pat. No. 6,552,841, the entire contents of which are incorporated herein by reference. The ultrasound camera was set-up evaluate crack detection using back-scattered energy.

Figure 9A:
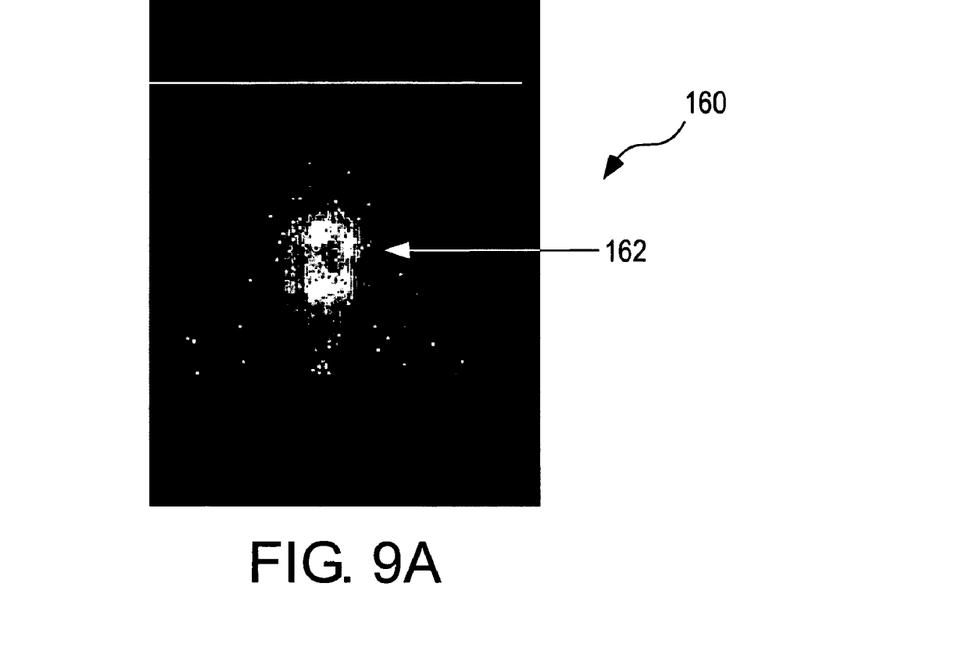
FIGS. 9A and 9B is an image obtained from the front surface of a square (no countersink) hole in a test sample with a front side crack.
Figure 9B:
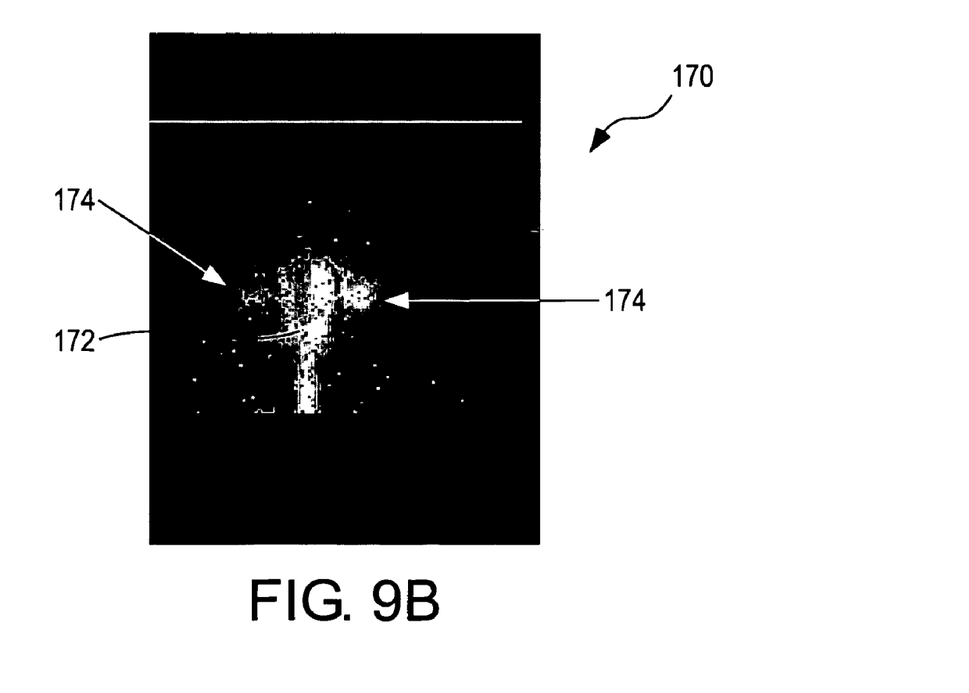

FIG. 9A is an image 160 obtained in Example Two. The image 160 was taken from the front surface of a square (no countersink) hole 162 in a structure with no cracks. FIG. 9B is an image 170 obtained in Example Two. The image 170 was taken from the front surface of a square (no countersink) hole 172 in a structure with cracks 174 on the rear side. In order to determine the depth of the crack 174, a technique called "range gating" was employed. In this technique, gating of the signal from the source transducer to the receiver was used similar to conventional thickness gage gating. The system has two types of control over the range gate. The first is the width of the acquisition window, or the total thickness that returns acoustic signals. The second is the delay from the front of the ultrasound camera to the target. Based on the 84 MHz clock in the ultrasound camera, gates can be changed down to twelve nanosecond increments. Other clock speeds can be used with attendant changes in the gates. At 5 MHz, the gate must be at least as wide as a full ultrasound period to capture the pulse. Assuming velocity of 3000 m/sec (the approximate acoustic shear wave velocity in aluminum) at 5 MHz, the full wave period of 0.20 microseconds equates to 0.0240 inches. The twelve nanosecond increment allows a delay change as small as 0.00144 inches (36 microns). Thus, the disclosed apparatus has an adequate z-axis (or depth) resolution to determine if the crack is just under the surface or on the front or back surface of lower layers.

Details of a suitable ultrasound camera for use in the apparatus and methods described herein are now presented. The ultrasound camera is a two-dimensional imaging system that creates real-time, high-resolution images of subsurface structures. A hybrid microelectronic array capable of generating ultrasound images with standard video presentation at video rates is used. Such an array is disclosed in U.S. Pat. No. 5,483,963, the entire contents of which are incorporated herein by reference, and is available for sale from Imperium, Inc., of Silver Spring, Md. Systems with the hybrid microelectronic array can be operated to detect ultrasound energy received in either a thru-transmission or pulse-echo modes.

The system operates by exciting a large area unfocused ultrasound transducer (used only as a source) that generates a collimated plane wave. The resultant pressure wave strikes the target and is scattered. An acoustic lens collects the scattered energy and focuses it onto an ultrasound sensitive detector array. The process can be used in either the thru-transmission (TT) mode or pulse echo (PE) mode. Typically, the ultrasound path is within a medium that allows its efficient (low-loss) transmission. For example, this medium is water or some other similar fluid. With some camera designs, the face of the camera is placed in intimate contact with the test object by means of a special acoustic coupling gel or compliant pads or membranes. For ultrasound methods based on shear waves, a shear wave adapter can be utilized as described herein.

The TT mode may be thought of as illuminating the test object with a "flashlight" of ultrasound. The TT mode generally provides a large amount of information and penetration of the test object with ultrasound. However, access to both sides of the test object is used in the TT mode. For the one-sided case, some form of the PE mode is used.

An exemplary array for incorporation into the camera is made up of two components, a Read Out Integrated Circuit (ROIC) and a piezoelectric material that is deposited onto the ROIC. The piezoelectric material is sensitive to ultrasound. Details of the ROIC can be found in U.S. Pat. No. 5,483,963, the entire contents of which are incorporated herein by reference. In one exemplary embodiment, the piezoelectric material is a 5-micron thick PVDF copolymer coated on the ROIC, e.g., spin coated. The material is made piezoelectric by, for example, an in-situ poling procedure. The individual electrodes of the array and a backside metallization define the individual elements of the ultrasound sensitive piezoelectric array. In another exemplary embodiment, the piezoelectric material is a piezoelectric ceramic coated on the ROIC. Exemplary embodiments of the array are 12 mm on a side made up of 120×120 pixel elements (14,400) with 100 micron center-to-center spacing. The energy that strikes the piezoelectric material creates voltages that are read out by a multiplexer, similar in operation to a video CCD imaging array. The array is responsive over a wide range of ultrasound frequencies, although most imaging is done between 1 MHz and 10 MHz.

The use of a lens in the ultrasound camera provides a simple, inexpensive alternative to complex beam forming often employed in ultrasound imaging. The user simply focuses by adjusting the lens while looking at the image on a monitor. Furthermore, the lens provides a means to trade off resolution and area coverage, or zoom in and out.

Like any imaging system, the defining characteristics are sensitivity, contrast resolution, dynamic range, and spatial resolution. Exemplary embodiments of the system and methods disclosed herein was tested to determine the ultrasound camera's ability to resolve small differences in detected signal level through the use of a medical phantom containing 3-mm and 5-mm spheres with small differences in attenuation from the surrounding background material. The ability to resolve amplitude differences is measured by calculating a Contrast to Noise Ratio (CNR), given by:

$$CNR=(I_s-I_b)/\sqrt{(\sigma_s^2+\sigma_b^2)/2} \tag{Eq. 2}$$

where $I_s$ and $I_b$ are sphere and background mean intensities and $\sigma_s$ and $\sigma_b$ are the respective standard deviations. In these measurements, statistics for a block of image pixels inside and outside each sphere area are collected and analyzed. Transmission images were obtained with an ultrasound camera as described herein, having a two-element aspheric 50 mm diameter F/1 lens, and a 5.4-MHz center frequency, 1.5 inch diameter pulsed transducer. FIGS. 10A-10D show the images taken of this phantom.

Table 1 summarizes some of the parameters of these images. The sphere diameters and their attenuations (dB/cm/MHz) are indicated in Table 1. The overall circular field of view indicates the beam diameter. Note the edges around the spheres. The pronounced edges are caused by a refraction edge effect that tends to enhance object resolvability. There are 256 grayscale levels to represent pixel intensities.

TABLE 1

Figure 10A:
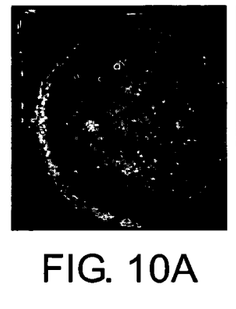
FIGS. 10A-10D show images taken of medical phantom containing 3-mm and 5-mm spheres with small differences in attenuation from the surrounding background material.
Figure 10B:
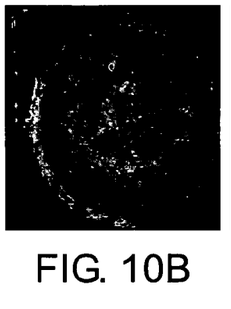
Figure 10C:
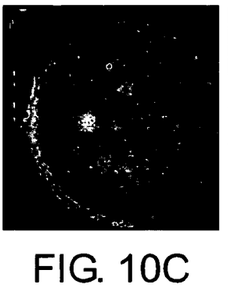
Figure 10D:
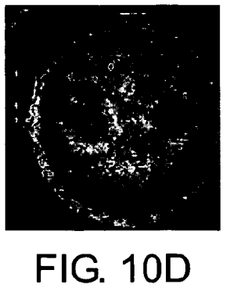

| Image | Sphere Diameter (mm) | Attenuation (dB/cm/MHz) |
|---|---|---|
| FIG. 10A | 3 | 0.06, 0.15 |
| FIG. 10B | 3 | 0.5, 0.8 |
| FIG. 10C | 5 | 0.06, 0.15 |
| FIG. 10D | 5 | 0.5, 0.8 |

Exemplary acoustic lenses for the ultrasound cameras are preferably diffraction limited. The equation below defines the limit of spatial resolution for the diffraction-limited lens used in the exemplary embodiments of the ultrasound camera and indicates that the resolution of the system should be approximately 500 µm:

$$D_L = 1.22 \lambda F/D$$

$\lambda = 277$ µm (5.4 MHz)

D=diameter of the aperture=diameter of the transducer=1.5"=3.75 cm

F=Focal Length=50 mm $D_L = 451$ µm

The spatial resolution test was conducted with a phantom with embedded calcium carbonate inclusions with diameters 150 to 160, 250 to 280, 320 to 355, 425 to 450, and 710 to 850 µm. Camera images are shown in FIGS. 11A-11C, where FIG. 11A is a 710 to 850 µm target group, FIG. 11B is a 425 to 450 µm target group and FIG. 11C is a 300 to 355 µm target group.

Figure 11A:
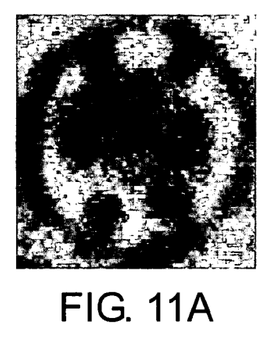
FIGS. 11A-11C are ultrasound camera images from a spatial resolution test conducted with a phantom with embedded calcium carbonate inclusions with various.
Figure 11B:
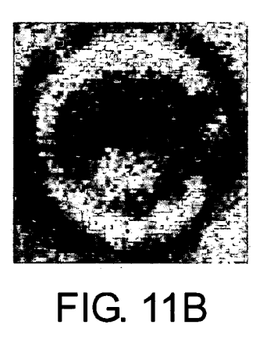
Figure 11C:
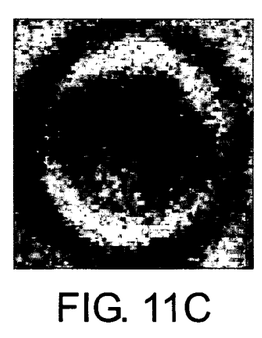

FIG. 11A clearly shows 700 µm targets. 700 µm is greater than the calculated resolution, and thus it is expected that the targets will be easily seen. FIG. 11B shows the presence of 450 µm targets, but the resolvability of the targets is strained. FIG. 11C shows the presence of 300 µm targets. The targets in this phantom are blurred as would be expected when the targets are smaller than the resolution limit.

Figure 12A:
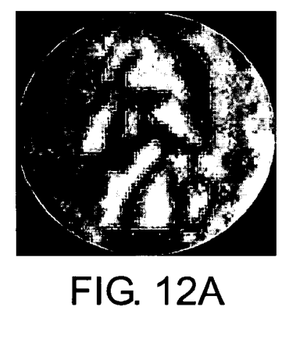
FIG. 12A and FIG. 12B show images taken by the imaging system disclosed herein using a 5 MHz source transducer and a two element F/1.0 acoustic lens.
Figure 12B:
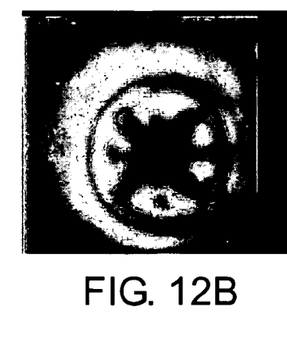

FIG. 12A and FIG. 12B show images taken by the imaging system disclosed herein using a 5 MHz source transducer and a two element F/1.0 acoustic lens. The face of George Washington on a quarter is quite visible in FIG. 12A, while the head of a fastener can be clearly seen in FIG. 12B. The images shown in FIGS. 12A and 12B are one frame of a 30 frame/second real time video output.

In another exemplary embodiment, the apparatus and methods disclosed herein can be used to produce a portable unit with a small display that creates an x-ray like image in real-time of a fastener and its immediate area. Such a unit would permit the operator to observe the region in real-time and visually identify flawed areas. If this device could detect cracks on the order of 0.030 inches, it would meet the demanding crack detection criteria, such as those of the armed services for in service equipment.

Figure 13:
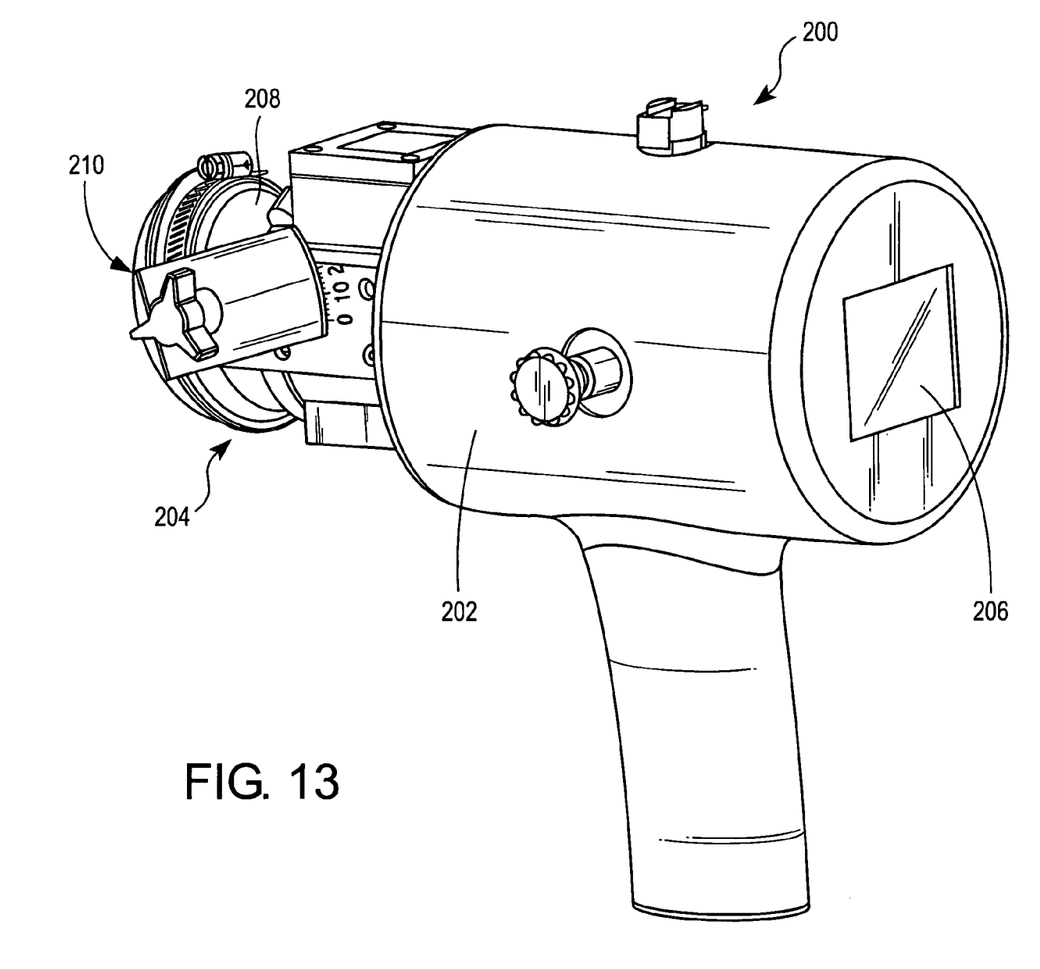
FIG. 13 is a schematic isometric illustration of an exemplary embodiment of a hand held device including an ultrasound camera with an adjustable angle adapter and an integrated viewing screen.

FIG. 13 is a schematic isometric illustration of an exemplary embodiment of a hand held device 200 including an ultrasound camera 202 with an adjustable angle adapter 204 and an integrated viewing screen 206. In the illustrated exemplary embodiment, the adjustable angle adapter 204 is mounted on the projecting end of the ultrasound camera 202 and is shown pivoting at about 15° from horizontal, although any suitable angle can be selected. The adjustable angle adapter 204 has gradations and/or markings to assist a user in adjusting the angle. Angles from 0° to 20° from horizontal are shown, but additional gradations and/or markings can be above or below the horizontal and can to any suitable range. To accommodate the angular adjustment of the adjustable angle adapter 204, a compliant boot 208 is placed about the periphery of the front coupling surface 210. The compliant boot 208 allows for movement of the front coupling surface 210 through the range of adjustable angles of the adjustable angle adapter 204 while still coupling the ultrasonic energy from the ultrasound camera 202 to the structure to be imaged. Additional connectors to the hand held device 200 can optionally include input and output connectors for control signals, imaging signals and other electronic inputs and outputs as desired by the application and the user.

Other applications for the apparatus and methods disclosed herein include fault imaging and periodic inspection, quality control uses, medical imaging and security imaging.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A system to obtain an ultrasonic image of a large detection area of a structure to be imaged, the system comprising:
   a source of ultrasound, the source of ultrasound includes a first transducer for generating an unfocused acoustic beam;
   an imaging array comprising a two dimensional array of acoustic to electrical transducers which produce electrical signals in response to an acoustic beam received by the imaging array; and
   an adapter ultrasonically coupling the source of ultrasound to a first surface of the structure to be imaged at an adjustable angle of incidence,
   wherein a first angle of incidence is selected to introduce a longitudinal wave into the structure, and
   wherein a second angle of incidence is selected to introduce a shear wave into the structure.

2. The system of claim 1, wherein an ultrasound camera includes the source of ultrasound and the imaging array, and wherein the adapter is interfaced to a projecting end of the ultrasound camera.

3. The system of claim 2, wherein the ultrasound camera and the adapter are part of a hand held device having an integrated viewing screen.

4. The system of claim 2, wherein the ultrasound camera and the adapter are mounted on a computer controlled scanning system.

5. The system of claim 1, wherein the first angle of incidence selected to introduce the longitudinal wave into the structure also is selected to substantially eliminate a detected signal from the shear wave.

6. The system of claim 5, wherein the second angle of incidence selected to introduce the shear wave into the structure is selected to substantially eliminate a detected signal from the longitudinal wave.

7. The system of claim 6, wherein the structure to be imaged is steel, a coupling medium is water and the first angle of incidence is about zero degrees and the second angle of incidence is about 18 degrees.

8. The system of claim 6, wherein the structure to be imaged is aluminum, a coupling medium is water and the first angle of incidence is about 0 degrees and the second angle of incidence is about 16.5 degrees.

9. The system of claim 3, wherein the large detection area is equal to or larger than one square inch.

10. The system of claim 9, wherein the large detection area is equal to or larger than two square inches.

11. The system of claim 10, wherein the large detection area is about three to four square inches.

12. The system of claim 1, further comprising means for viewing the ultrasonic image.

13. The system of claim 12, wherein means for viewing is a LCD, a monitor, or a computer monitor.

14. A system to obtain an ultrasonic image of a large detection area of a structure to be imaged, the system comprising:
   a source of ultrasound;
   an imaging array comprising a two dimensional array of acoustic to electrical transducers which produce electrical signals in response to an acoustic beam received by the imaging array; and
   an adapter ultrasonically coupling the source of ultrasound to a first surface of the structure to be imaged at an adjustable angle of incidence,
   wherein a first angle of incidence is selected to introduce a longitudinal wave into the structure,
   wherein a second angle of incidence is selected to introduce a shear wave into the structure, and
   wherein the system obtains a real time C-scan image and a real time A-scan image, the C-scan image is produced from a first detection signal from a first group of transducers of the imaging array and the A-scan image is produced from a second detection signal from a second group of transducers of the imaging array.

15. A method of ultrasonic imaging a structure, comprising:
   ultrasonically coupling a source of ultrasonic energy to a first surface of a structure to be imaged with an adapter, the source of ultrasound energy includes a first transducer for generating an unfocused acoustic beam, the adapter adjustable to select a first angle of incidence and a second angle of incidence;
   projecting ultrasonic energy into the structure at a selected angle of incidence; and
   detecting a reflected acoustic energy from the structure with an ultrasound camera, the ultrasound camera including an imaging array comprising a two dimensional array of acoustic to electrical transducers which produce electrical signals in response to the acoustic energy received by the imaging array,
   wherein the signals produce a real time C-scan image of a detection area equal to or larger than one square inch,
   wherein the first angle of incidence is selected to introduce a longitudinal wave into the structure, and
   wherein the second angle of incidence is selected to introduce a shear wave into the structure.

16. The method of claim 15 wherein the first angle of incidence selected to introduce the longitudinal wave into the structure also is selected to substantially eliminate a detected signal from the shear wave.

17. The method of claim 16, wherein the second angle of incidence selected to introduce the shear wave into the structure is selected to substantially eliminate a detected signal from the longitudinal wave.

18. The method of claim 17, wherein the structure to be imaged is steel, a coupling medium water and the first angle of incidence is about 0 degrees and the second angle of incidence is about 18 degrees.

19. The method of claim 17, wherein the structure to be imaged is aluminum, a coupling medium is water and the first angle of incidence is about 0 degrees and the second angle of incidence is about 16.5 degrees.

20. The method of claim 15, wherein the detection area is about three to four square inches.

21. The method of claim 15, comprising electronically gating the received acoustic energy to filter multiple signals.

22. The method of claim 15, wherein the signals produce a real time A-scan image of a portion of the detection area.

23. The method of claim 15, comprising viewing the ultrasonic image.

24. The method of claim 23, wherein the ultrasonic image is an image on a LCD, a monitor, or a computer monitor.

25. The method of claim 23, wherein the ultrasound camera and the adapter are part of a hand held device having an integrated viewing screen.

26. The method of claim 23, comprising positioning the source of ultrasonic energy, the adapter and the ultrasound camera with a computer controlled scanning system.

27. The method of claim 15, wherein the method is a pitch-catch method.

28. The method of claim 15, wherein the method is a through transmission method.

29. A method of ultrasonic imaging a structure, comprising:
   ultrasonically coupling a source of ultrasonic energy to a first surface of a structure to be imaged with an adapter, the adapter adjustable to select a first angle of incidence and a second angle of incidence;
   projecting ultrasonic energy into the structure at a selected angle of incidence; and
   detecting a reflected acoustic energy from the structure with an ultrasound camera, the ultrasound camera including an imaging array comprising a two dimensional array of acoustic to electrical transducers which produce electrical signals in response to the acoustic energy received by the imaging array,
   wherein the signals produce a real time A-scan image and a real time C-scan image of a detection area equal to or larger than one square inch,
   the C-scan image is produced from a first detection signal from a first group of transducers of the imaging array and the A-scan image is produced from a second detection signal from a second group of transducers of the imaging array,
   wherein the first angle of incidence is selected to introduce a longitudinal wave into the structure, and
   wherein the second angle of incidence is selected to introduce a shear wave into the structure.

* * * * *